(12) United States Patent
Zhang et al.

(10) Patent No.: US 8,324,429 B2
(45) Date of Patent: Dec. 4, 2012

(54) PREPARATION METHOD OF RIVASTIGMINE, ITS INTERMEDIATES AND PREPARATION METHOD OF THE INTERMEDIATES

(75) Inventors: Fuli Zhang, Shanghai (CN); Meng Hu, Shanghai (CN); Meihua Xie, Shanghai (CN); Anping Lai, Taizhou (CN); Rentong Sun, Taizhou (CN); Daoxin Chen, Taizhou (CN); Rusheng Bao, Taizhou (CN); Hua Bai, Taizhou (CN)

(73) Assignees: Shanghai Institute of Pharmaceutical Industry (CN); Zhejian Hisun Pharmaceutical Co., Ltd. (CN)

( * ) Notice: Subject to any disclaimer, the term of this patent is extended or adjusted under 35 U.S.C. 154(b) by 284 days.

(21) Appl. No.: 12/812,347

(22) PCT Filed: Jan. 10, 2008

(86) PCT No.: PCT/CN2008/000072
§ 371 (c)(1),
(2), (4) Date: Jul. 9, 2010

(87) PCT Pub. No.: WO2009/086705
PCT Pub. Date: Jul. 16, 2009

(65) Prior Publication Data
US 2010/0286437 A1 Nov. 11, 2010

(51) Int. Cl.
*C07C 211/03* (2006.01)
*C07C 269/04* (2006.01)
(52) U.S. Cl. ......... 564/384; 564/389; 560/133; 560/136
(58) Field of Classification Search .................. 564/384, 564/389; 560/133, 136
See application file for complete search history.

(56) References Cited

U.S. PATENT DOCUMENTS 5,602,176 A  2/1997  Enz

FOREIGN PATENT DOCUMENTS

| CN | 200710067343 |   | 5/2007 |
| CN | 200610116949 |   | 4/2008 |
| DE | 3805744 | * | 9/1988 |
| EP | 0257787 |   | 3/1988 |
| GB | 2409543 |   | 6/2005 |
| IN | 747/MUM/2005 |   | 6/2007 |
| IN | 246030 | * | 2/2011 |
| WO | WO03/101917 |   | 12/2003 |
| WO | WO2004/037771 |   | 5/2004 |
| WO | WO2006/048720 |   | 5/2006 |
| WO | WO2006/068386 |   | 6/2006 |
| WO | WO2007/014973 |   | 2/2007 |

OTHER PUBLICATIONS

Ciszewska, Grazyna, et al., *Synthesis of Tritium, Deuterium, and Carbon-14 Labeled (S)-N-Ethysl-N-methyl-3[1-(dimethylamino)ethyl]carbamic acid, phenyl ester, (L)-2,3-dihydrozybuanedioic acid salt (SDZ ENA 713 hta), and Investigational Drug for the Treatment of Alzheimer's Disease*, Journal of Labelled Compounds and Radiopharmaceuticals, 1997, pp. 651-668, 39(8).

Clarke, H.T., et al., *The Action of Formaldehyde on Amines and Amino Acids*, Journal of the American Chemical Society, 1933, pp. 4571-4587, 55(11).

Eleveld, M.B., et al., *Diastereoselective Synthesis of Chiral Secondary Amines with Two Chiral Centers Directly Attached to the Nitrogen Atom*, Journal of Organic Chemistry, 1986, pp. 9635-3642, 51.

Gribble, Gordon W., et al., *Reactions of Sodium Borohydride in Acidic Media. I. Reduction of Indoles and Alkylation of Aromatic Amines with Carboxylic Acids*, Journal of the American Chemical Society, 1974, pp. 7812-7814, 96(25).

Hu, Meng, et al., *A Simple and Efficent Synthesis of (S)- and (R)-1-(3-Methoxyphenyl) Ethylamine*, Letters in Organic Chemistry, 2007, pp. 126-128, vol. 4, No. 2.

Pyocyanine, Organic Synthesis, Coll. vol. 3, p. 753 (1955); vol. 26, p. 86 (1946).

Quinacetophenone Monomethyl Ether, Organic Syntheses, Coll. vol. 4, p. 836 (1963); vol. 31, p. 90 (1951).

Yong-Wen, Jiang, et al., *The Synthesis of Rivastigmine, A Chiral Drug for AD*, Journal of East China Normal University (Natural Science), 2001, pp. 61-65, vol. 1.

* cited by examiner

Primary Examiner — Shailendra Kumar

(57) ABSTRACT

The present invention provides N-methylethylcarbamino-3-[(S)-1-(methyl-[(S)-1-phenylethyl]amino)ethyl]phenyl ester represented by formula (II) and its preparation method. The present invention also provides (S)-1-(3-methoxyphenyl)-N-methyl-N—[(S)-1-phenylethyl]ethylamine and 3-[(S)-1-(methyl-[(S)-1-phenylethyl]amino)ethyl]phenol as intermediates of the compound represented by formula (II), and the use of the compound represented by formula (II) for preparing rivastigmine used for treating Alzheimer disease.

6 Claims, No Drawings

PREPARATION METHOD OF RIVASTIGMINE, ITS INTERMEDIATES AND PREPARATION METHOD OF THE INTERMEDIATES

CROSS REFERENCE TO RELATED APPLICATION

This application is a 35 U.S.C. §371 national phase application of PCT Application No. PCT/CN2008/000072, filed on Jan. 10, 2008, the disclosures and contents of which are hereby incorporated by reference as if recited in full herein. The above-referenced PCT International Application was published in Chinese as International Publication No. WO 2009/086705 A1.

FIELD OF THE INVENTION

The present invention is related to N-methylethylcarbamino-3-[(S)-1-(methyl-[(S)-1-phenylethyl]amino) ethyl] phenyl ester (the compound represented by formula (II)) and its process of preparation. The present invention further describes (S)-1-(3-methoxyphenyl)-N-methyl-N—[(S)-1-phenylethyl]ethylamine and 3-[(S)-1-(methyl-[(S)-1-phenylethyl]amino) ethyl]phenol as intermediates for preparing the compound represented by formula (II), and the use of the compound represented by formula (II) for preparing rivastigmine which is used for treating Alzheimer disease.

BACKGROUND OF THE INVENTION

It has been proved that rivastigmine has the activity of selective inhibitive central cholinesterase so that it is used for treating presenile dementia. The structure of rivastigmine is shown as formula (VIII):

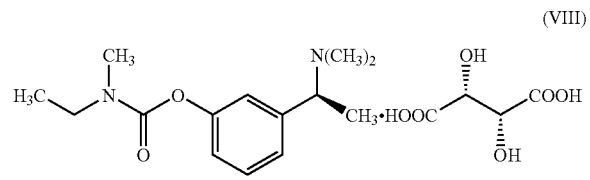

(VIII)

The synthesis of rivastigmine was reported in U.S. Pat. No. 5,602,176, GB2409453, and Yonwen, Jiang et. al. [Journal of East China Normal University (Natural Science), 2001, 1, 61-65], in which the method is disclosed as: preparing racemic rivastigmine by a series of reactions, then salifying the result with D-(+)-O, o'-bis-p-tolyl formacyl tartaric acid monohydrate (D-DTTA) to separate the racemic mixture, and recrystallizing at least three time to obtain (S)-rivastigmine with an optical purity of above 99%. The final yield is only 5.14%.

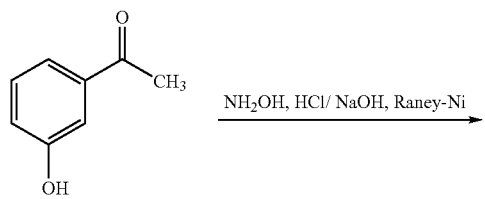

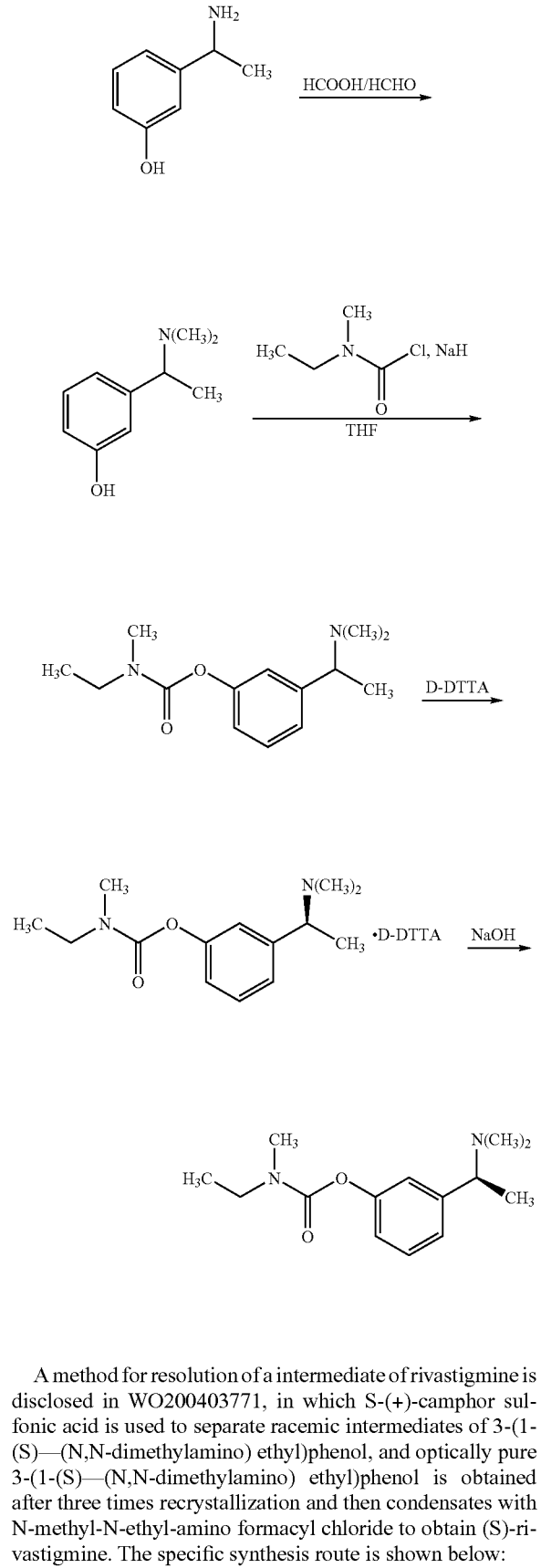

A method for resolution of a intermediate of rivastigmine is disclosed in WO200403771, in which S-(+)-camphor sulfonic acid is used to separate racemic intermediates of 3-(1-(S)—(N,N-dimethylamino) ethyl)phenol, and optically pure 3-(1-(S)—(N,N-dimethylamino) ethyl)phenol is obtained after three times recrystallization and then condensates with N-methyl-N-ethyl-amino formacyl chloride to obtain (S)-rivastigmine. The specific synthesis route is shown below:

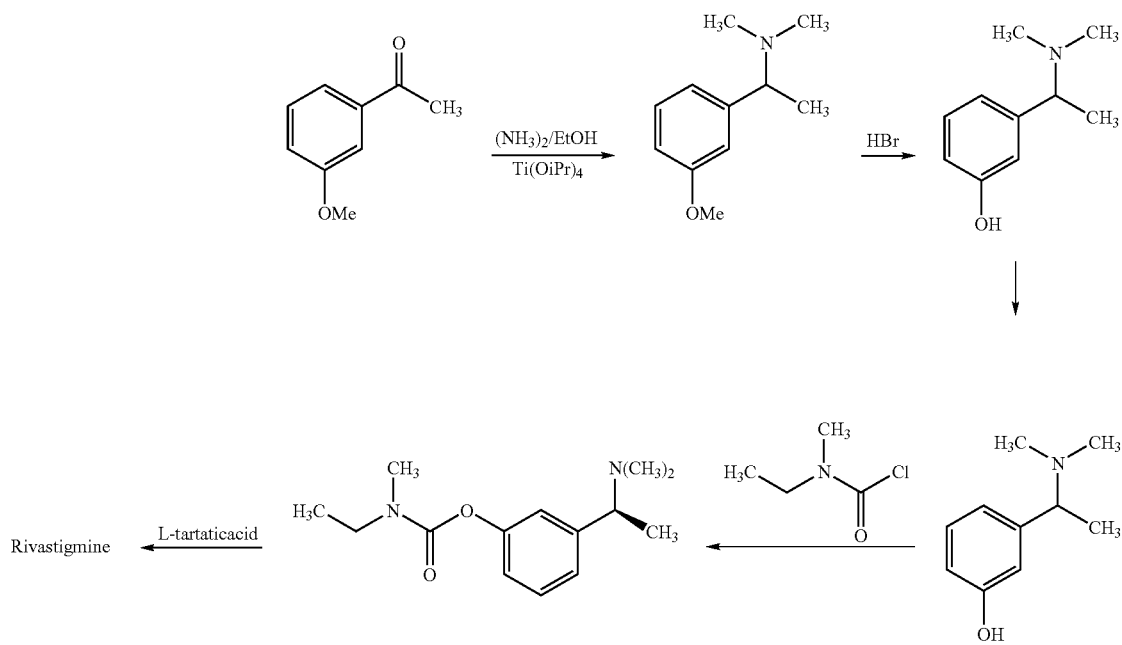

A method for resolution of a intermediate of rivastigmine is also disclosed in WO2007014973, in which S-(+)-camphor sulfonic acid is used to separate racemic intermediates of 3-(1-(methylamino) ethyl)phenol, and the result condensates with N-methyl-N-ethyl-amino formacyl chloride to obtain N-methylethylcarbamino-3-[(S)-1-(methylamino)-ethyl] phenyl ester, and a methylation is then performed on the nitrogen atom followed by salifying with L-(+)-tartaric acid so that rivastigmine is obtained. The methylation needs a reduction system of sodium cyanoborohydride/formaldehyde, in which sodium cyanoborohydride is highly toxic, so that the method is not suitable for industrial production. The specific synthesis route is shown below:

The resolution methods mentioned above are time consuming with low yields, so that final yields are reduced and costs are increased, which are not beneficial for industrial production and the optical purity of rivastigmine cannot be guaranteed.

SUMMARY OF THE INVENTION

The present invention provides a compound having a structure represented by formula (IV) below, i.e. [(S)-1-(3-methoxyphenyl)-N-methyl-N—[(S)-1-phenylethyl]ethylamine]:

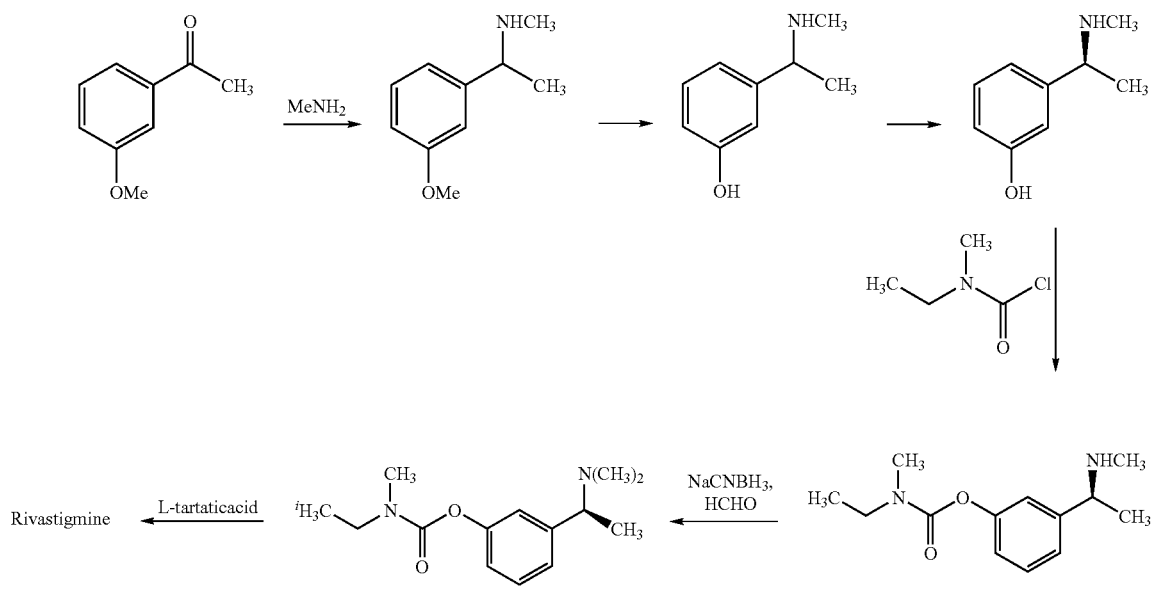

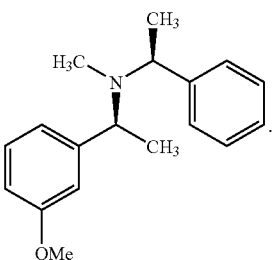

The present invention also provides a compound having a structure represented by formula (V) below, i.e. [3-[(S)-1-(methyl-[(S)-1-phenylethyl]amino) ethyl]phenol]:

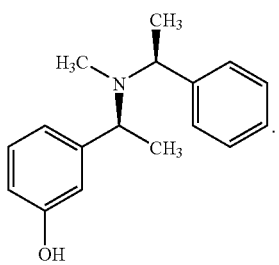

The present invention also provides a compound having a structure represented by formula (II) below, i.e. [N-methyl-ethylcarbamino-3-[(S)-1-(methyl-[(S)-1-phenylethyl]amino) ethyl]phenyl ester]:

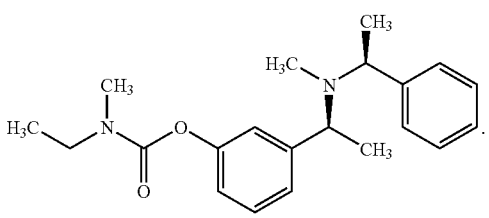

The compound represented by formula (IV) and the compound represented by formula (V) above are key intermediates for the preparation of the compound represented by formula (II).

The present invention further provides a preparation method of the compound represented by formula (II) comprising the steps of:

a) methylating a compound having a structure represented by formula (III) below, i.e. [(S)-1-(3-methoxyphenyl)-N—((S)-1-phenylethyl)ethylamine], to obtain a compound represented by formula (IV);

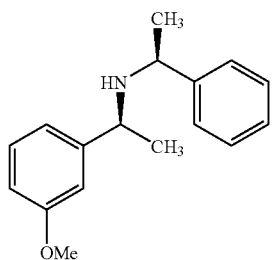

b) demethylating the compound represented by formula (IV) to obtain the compound represented by formula (V); and c) carrying out a condensation reaction of the compound represented by formula (V) and N-methyl-N-ethyl-amino formacyl chloride to provide the compound represented by formula (II).

In some embodiments, in step a), there may be two possible approaches for the methylation reaction:

In one embodiment, the first approach: Reductive N-methylation is performed using formaldehyde in the presence of a reducing agent. In one embodiment, (S)-1-(3-methoxyphenyl)-N—((S)-1-phenylethyl)ethylamine as a raw material, and formic acid or a borohydride of a metal of group I or group II as a reducing agent react with formaldehyde to perform the reductive N-methylation reaction, and (S)-1-(3-methoxyphenyl)-N-methyl-N—[(S)-1-phenylethyl]ethylamine is obtained. When formic acid is used as the reducing agent, the reaction is Eschweiler-Clarke reaction, the process of which is simple and common in the art. See J. Am. Chem. Soc., 1933, 55, 4571, which is incorporated herewith by reference. When the borohydride of a metal of group I or group II is used as the reducing agent, the reaction is usually performed in an aqueous solution, acetic acid and sodium acetate are used as a buffer, and a mixture of (S)-1-(3-methoxyphenyl)-N—((S)-1-phenylethyl)ethylamine and formaldehyde are added in batches into the borohydride under cooling. See J. Am. Chem. Soc., 1974, 96, 7812, which is incorporated herewith by reference in its entirety.

In another embodiment, the second approach: The methylation reaction is carried out using (S)-1-(3-methoxy phenyl)-N—((S)-1-phenylethyl)ethylamine as a raw material, and methyl iodide or dimethyl sulfate as a methylation agent, so as to obtain (S)-1-(3-methoxyphenyl)-N-methyl-N—[(S)-1-phenylethyl]ethylamine. Methyl iodide or dimethyl sulfate are conventional methylation agents, and the method is common in the art. See OS, CV4, 836 (1963); OS, CV3, 753 (1955), which are incorporated herewith by reference in their entireties.

In step b), said demethylation reaction may be performed in hydrobromic acid. In some embodiments, a phase-transfer catalyst may be added during the demethylation reaction to accelerate the reaction. The phase-transfer catalyst may be any one selected from tetrabutyl ammonium bromide, tetraethyl ammonium bromide, tetrabutyl ammonium iodide or triethyl benzyl ammonium chloride. See J Labelled Compd. Radiophatin, 1997, 39(8): 651-668, which is incorporated herewith by reference in its entirety.

In step c), at least one basic reagent may be added during the condensation reaction. The basic reagent may be one or more of the following compounds: inorganic basic compounds selected from sodium carbonate, potassium carbonate, sodium amide, sodium hydride; alkali metal alcohol-based compounds selected from sodium methanol, sodium ethanol, potassium t-butanol; organic basic compounds selected from triethylamine, pyridine, quinoline, diisopropylethylamine. In some embodiments, at least one inert solvent is used as a solvent in the condensation reaction. The inert solvent may include, but is not limited to, any of ether-based solvents selected from tetrahydrofuran, ethyl ether, ethylene glycol dimethyl ether, dioxane, dimethyl tetrahydrofuran; aromatic hydrocarbon-based solvents selected from benzene, toluene, xylene; halogenated hydrocarbon-based solvents selected from dichloromethane, trichloromethane, dichloroethane; dimethylformamide, dimethyl acetamide and acetone. See WO2004/037771 and WO2006/068386, which are incorporated herewith by reference in their entireties. In some embodiments, a phase-transfer catalyst may be added during the condensation reaction. The phase-transfer catalyst may include, but is not limited to, any of tetrabutyl ammonium bromide, tetraethyl ammonium bromide, tetrabutyl ammonium iodide or triethyl benzyl ammonium chloride.

The present invention also provides a process of preparing a compound having the structure represented by formula (VIII) below, i.e. rivastigmine:

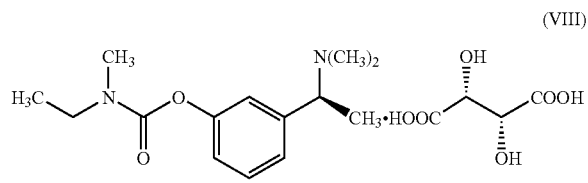

comprising the steps of:

a) debenzylating the compound represented by formula (II) to obtain a compound having the structure represented by formula (VI) below, i.e. [N-methylethylcarbamino-3-[(S)-1-(methylamino) ethyl]phenyl ester];

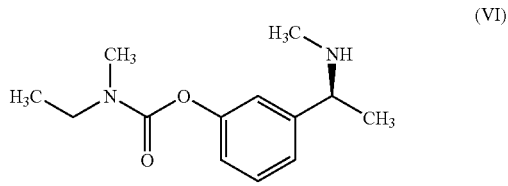

b) methylating the compound represented by formula (VI) to obtain a compound having the structure represented by formula (VII) below, i.e. [N-methylethylcarbamino-3-[(S)-1-(dimethylamino) ethyl]phenyl ester];

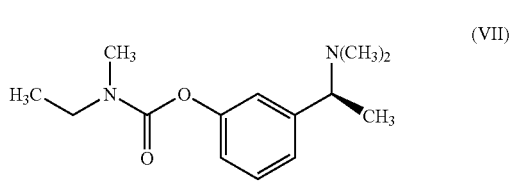

c) reacting the compound represented by formula (VII) with L-(+)-tartaric acid to provide the compound represented by formula (VIII).

In step a), palladium-carbon hydrogenation catalyst in an amount ranging from 2% to 50% is used in the debenzylation reaction under a pressure ranging from 1 to 40 atm. In one embodiment, the pressure for the debenzylation reaction is ranging from 3 to 30 atm, and at a reaction temperature ranging from 20° C. to 100° C., or from 40° C. to 80° C. An organic solvent used in the reaction may be an alcohol selected from methanol, ethanol, propanol, isopropanol, butanol and t-butanol; or an ether selected from ethyl ether, isopropyl ether, tetrahydrofuran; or any mixtures of above said solvents. See EP257787, which is incorporated herewith by reference in its entirety.

In step b), the method for the methylation reaction is the same as that used for preparing the compound represented by formula (IV), In some embodiments, the methylation uses Eschweiler-Clarke reaction or methyl iodide or dimethyl sulphate is used as a methylating agent in the methylation reaction.

The compound represented by formula (VII) may react with L-(+)-tartaric acid according to conventional processes so as to obtain the compound represented by formular (VIII).

The present application describes that the preparation of (S)-1-(3-methoxyphenyl)-N—((S)-1-phenylethyl)ethylamine (i.e, the compound represented by formula (III)) or the salt thereof. An asymmetric reductive amination reaction is performed using o-methoxyl acetophenone and S-α-phenylethylamine in ethyl acetate in the presence of the reduction system of tetraiospropyl titanate/Raney-Ni/$H_2$ to obtain the compound of formula (III). See J. Org. Chem., 1986, 51, 3635; Letters in Organic Chemistry, 2007, 4(2), 126-128; and Chinese patent application No. 200610116949.3, which are incorporated herewith by reference in their entireties. Based on the above, the benzyl of the compound represented by formula (III) or its salt is not removed, and methylation by multiple steps is used to prepare rivastigmine. The compounds represented by formulas (IV), (V) and (II) of the present invention are isomers with single configuration, which can be conveniently purified by utilizing the differences between the compounds and impurities which are not enantiomers thereof.

The synthesis process of the invention for preparing rivastigmine is reasonably designed and is very simple. In addition, raw materials can be easily obtained. The process avoids a waste caused by optical resolutions and has a high final yield (above 45% with respect to the compound represented by formula (III)). The product, rivastigmine, has a high chemical and optical purity (HPLC purity is above 99.7%, optical purity is above 99.8%). Therefore, the process can be easily industrialized for mass production.

DETAILED DESCRIPTION OF THE INVENTION

The present invention will be further illustrated below in conjunction with examples, which do not form any limitation to the invention.

$^1$H-NMR is measured by AM 400 nuclear magnetic resonance analyzer, chemical shift is represented by δ (ppm). Mass spectrum is measured by Shimadzu LCMS-2010 mass spectrometer, Optical rotation is measured by Perkin-Elmer 341 polarimeter,

EXAMPLE 1

Preparation of (S)-1-(3-methoxyphenyl)-N-methyl-N—[(S)-1-phenylethyl]ethylamine (the compound represented by formula (IV))

38 g (0.149 mol) (S)-1-(3-methoxyphenyl)-N—((S)-1-phenylethyl)ethylamine (the compound represented by formula (III)) and 27.42 g (0.596 mol) formic acid were mixed at room temperature, and then 24.84 g (0.298 mol) formaldehyde aqueous (37 mass %) was added therein. The mixture was fluxed for 5 hours. After the mixture was cooled to room temperature, 265 ml water was added followed by adding sodium carbonate (20.33 g) in batches. Then the result was extracted with 250 ml ethyl acetate twice. The combined organic layers was washed with 50 ml water, and then dried with anhydrous magnesium sulfate. Colorless liquid (40.2 g) was obtained after filtering and recovering the solvent under a reduced pressure, which was used directly for the next reaction.

Optical rotation $[\alpha]^{20}_D = -75.6°$, C=2, ethanol.

$^1$H NMR (CDCl$_3$) δ ppm: 1.33 (q, 6H), 2.01 (s, 3H), 3.82 (s+m, 5H), 6.86 (m, 1H), 6.95 (m, 2H), 7.25 (m, 2H), 7.33 (m, 4H); MS (ESI) m/z: 270.2 (M$^+$+1).

EXAMPLE 2

Preparation of 3-[(S)-1-(methyl-[(S)-1-phenylethyl] amino) ethyl]phenol (the compound represented by formula (V))

After 34.67 g (129 mmol) the compound represented by formula (IV) and 93 ml hydrobromic acid (with a content above 40 mass %) were mixed, the mixture was fluxed for 10 hours. After the mixture was cooled to room temperature, 150 ml water and 370 ml ethyl acetate were added therein followed by adding sodium carbonate in batches to adjust pH to 8. The water layer was separated, and extracted with 150 ml ethyl acetate twice. Then the combined organic layers was washed with 50 ml water twice, and dried with anhydrous magnesium sulfate. After filtering and recovering the solvent under a reduced pressure, the crude product was recrystallized with isopropyl ether to obtain white solid (25.25 g) with a yield of 76.84%.

Optical rotation $[\alpha]^{20}_D = -82.5°$, C=2, ethanol; mp 99-100.
$^1$H NMR (CDCl$_3$) δ ppm: 1.32 (q, 6H), 2.00 (s, 3H), 3.78 (q, 1H), 3.86 (q, 1H), 6.70 (m, 1H), 6.91 (m, 2H), 7.20 (m, 2H), 7.33 (m, 4H); MS (ESI) m/z: 256.1 (M$^+$+1).

EXAMPLE 3

Preparation of 3-[(S)-1-(methyl-[(S)-1-phenylethyl] amino) ethyl]phenol (the compound represented by formula (V))

After 34.67 g (129 mmol) the compound represented by formula (IV) and 93 ml hydrobromic acid (with a content above 40 mass %) were mixed, 2.08 g (6.4 mmol) tetrabutyl ammonium bromide was added therein, and then the mixture was fluxed for 6 hours. After the mixture was cooled to room temperature, 150 ml water and 370 ml ethyl acetate were added therein, followed by adding sodium carbonate in batches to adjust pH to 8. The water layer was separated and extracted with 150 ml ethyl acetate twice. Then the combined organic layers was washed with 50 ml water twice, and dried with anhydrous magnesium sulfate. After filtering and recovering the solvent under a reduced pressure, the crude product was recrystallized with isopropyl ether to obtain white solid (26.3 g) with a yield of 80%.

Optical rotation $[\alpha]^{20}_D = -82.5°$, C=2, ethanol; mp 99-100.
$^1$H NMR (CDCl$_3$) δ ppm: 1.32 (q, 6H), 2.00 (s, 3H), 3.78 (q, 1H), 3.86 (q, 1H), 6.70 (m, 1H), 6.91 (m, 2H), 7.20 (m, 2H), 7.33 (m, 4H); MS (ESI) 256.1 (M$^+$+1).

EXAMPLE 4

Preparation of N-methylethylcarbamino-3-[(S)-1-(methyl-[(S)-1-phenylethyl]amino) ethyl]phenyl ester (the compound represented by formula (II))

Under nitrogen atmosphere protection, 10 g (39.2 mmol) the compound represented by formula (V) was solved in 80 ml dried tetrahydrofuran, and 3.14 g (78.4 mmol) sodium hydride (60 mass %) was added therein in batches at a temperature of 20 of the solution. The solution was then stirred for a half hour at room temperature. A mixture of 9.53 g (78.4 mmol) N-ethyl-N-methylamino formacyl chloride and 20 ml tetrahydrofuran was dropped into the solution, and after that the reaction was stirred for 2 hours at room temperature. The solvent was recovered under a reduced pressure. Then, 120 ml water was added, and the result was extracted with 100 ml ethyl acetate twice. The combined organic layers was washed with 30 ml sodium hydroxide aqueous (0.1N) twice, and then dried with anhydrous magnesium sulfate. Liquid (15.22 g) was obtained after filtering and recovering the solvent under a reduced pressure, which was used directly for the next reaction.

Optical rotation $[\alpha]^{20}_D = -65.9°$, C=1, ethanol.
$^1$H NMR (CDCl$_3$) δ ppm: 1.25 (d, 3H), 1.33 (q, 6H), 2.00 (s, 3H), 3.04 (d, 3H), 3.46 (s, 2H), 3.84 (m, 2H), 7.05 (m, 1H), 7.27 (m, 8H); MS (ESI) m/z: 341.2 (M$^+$+1).

EXAMPLE 5

Preparation of N-methylethylcarbamino-3-[(S)-1-(methyl-[(S)-1-phenylethyl]amino) ethyl]phenyl ester (the compound represented by formula (II))

Under nitrogen atmosphere protection, 10 g (39.2 mmol) the compound represented by formula (V) was solved in 80 ml acetone, and 0.63 g (47.1 mmol) N-ethyl-N-methylamino formacyl chloride and 2.08 g (1.96 mmol) tetrabutyl ammonium bromide were added therein. The solution was refluxed for 10 hours followed by recovering the solvent under a reduced pressure and then adding 120 ml water, The result was extracted with 100 ml ethyl acetate twice. The combined organic layers was washed with 30 ml sodium hydroxide aqueous (0.1N) twice and then dried with anhydrous magnesium sulfate, Liquid (14.79 g) was obtained after filtering and recovering the solvent under a reduced pressure, which was used directly for the next reaction.

Optical rotation $[\alpha]^{20}_D = -65.9°$, C=1, ethanol.
$^1$H NMR (CDCl$_3$) δ ppm: 1.25 (d, 3H), 1.33 (q, 6H), 2.00 (s, 3H), 3.04 (d, 3H), 3.46 (s, 2H), 3.84 (m, 2H), 7.05 (m, 1H), 7.27 (m, 8H); MS (ESI) m/z: 341.2 (M$^+$+1).

EXAMPLE 6

Preparation of N-methylethylcarbamino-3-[(S)-1-(methylamino) ethyl]phenyl ester (the compound represented by formula (VI))

15.22 g (39.2 mmol) the compound represented by formula (II), 120 ml methanol and 1.33 g Pd/C (10 mass %) were fed in a 250 ml hydrogenation reactor which was set to 10 atm, and reacted for 12 hours with an inner temperature of 60. The product was discharged from the reactor and Pd/C was removed by filtering. Liquid (11.27 g) was obtained after recovering the solvent under a reduced pressure, which was used directly for the next reaction.

Optical rotation $[\alpha]^{20}_D = -32.7°$, C=1, ethanol.
$^1$H NMR (CDCl$_3$) δ ppm: 1.24 (m, 3H), 1.43 (q, 3H), 2.31 (s, 3H), 3.02 (d, 3H), 3.44 (s, 2H), 3.64 (m, 1H), 6.98 (m, 1H), 7.01 (m, 1H), 7.10 (m, 1H), 7.28 (m, 1H); MS (ESI) m/z: 237.1 (M$^+$+1).

EXAMPLE 7

Preparation of N-methylethylcarbamino-3-[(S)-1-(methylamino) ethyl]phenyl ester (the compound represented by formula (VI))

15.22 g (39.2 mmol) the compound represented by formula (II), 120 ml tetrahydrofuran and 1.33 g Pd/C (10 mass %) were fed in a 250 ml hydrogenation reactor which was set to 5 atm, and reacted for 16 hours with an inner temperature of 40. The product was discharged from the reactor and Pd/C was removed by filtering. Liquid (11.36 g) was obtained after recovering the solvent under a reduced pressure, which was used directly for the next reaction.

Optical rotation $[\alpha]^{20}_D = -32.7°$, C=1, ethanol.

$^1$H NMR (CDCl$_3$) δ ppm: 1.24 (m, 3H), 1.43 (q, 3H), 2.31 (s, 3H), 3.02 (d, 3H), 3.44 (s, 2H), 3.64 (m, 1H), 6.98 (m, 1H), 7.01 (m, 1H), 7.10 (m, 1H), 7.28 (m, 1H); MS (ESI) m/z: 237.1 (M$^+$+1).

EXAMPLE 8

Preparation of N-methylethylcarbamino-3-[(S)-1-(methylamino) ethyl]phenyl ester (the compound represented by formula (VI))

15.22 g (39.2 mmol) the compound represented by formula (II), 120 ml ethanol and 2.66 g Pd/C (5 mass %) were fed in a 250 ml hydrogenation reactor which was set to 20 atm, and reacted for 10 hours with an inner temperature of 80. The product was discharged from the reactor and Pd/C was removed by filtering. Liquid (11.45 g) was obtained after recovering the solvent under a reduced pressure, which was used directly for the next reaction.

Optical rotation $[\alpha]^{20}_D = -32.7°$, C=1, ethanol.

$^1$H NMR (CDCl$_3$) δ ppm: 1.24 (m, 3H), 1.43 (q, 3H), 2.31 (s, 3H), 3.02 (d, 3H), 3.44 (s, 2H), 3.64 (m, 1H), 6.98 (m, 1H), 7.01 (m, 1H), 7.10 (m, 1H), 7.28 (m, 1H); MS (ESI) m/z: 237.1 (M$^+$+1).

EXAMPLE 9

Preparation of N-methylethylcarbamino-3-[(S)-1-(dimethylamino) ethyl]phenyl ester (the compound represented by formula (VII))

11.27 g (39.2 mmol) the compound represented by formula (VI) obtained in Example 4 and 7.22 g (157 mmol) formic acid were mixed at room temperature, and then 6.54 g (78.4 mmol) formaldehyde aqueous solution (37 mass %) was added. The mixture was fluxed for 2 hours, and then cooled to room temperature. 50 ml water was added, followed by adding sodium carbonate in batches to adjust pH to 8. The result was then extracted with 60 ml ethyl acetate twice. The combined organic layers was washed with 15 ml water, and then dried with anhydrous magnesium sulfate. Colorless liquid (11.3 g) was obtained after filtering and recovering the solvent under a reduced pressure.

Vacuum distillation: 1 to 1.5 kpa, the fraction at a temperature ranging from 128 to 133 is collected, and 7.77 g product is obtained with a yield of 79.3%.

Optical rotation $[\alpha]^{20}_D = -32.1°$, C=5, ethanol.

$^1$H NMR (CDCl$_3$) δ ppm: 1.22 (m, 3H), 1.35 (q, 3H), 2.20 (s, 6H), 3.02 (d, 3H), 3.25 (m, 1H), 3.44 (s, 2H), 7.05 (m, 3H), 7.27 (m, 1H); MS (ESI) m/z: 251.2 (M$^+$+1).

EXAMPLE 10

Preparation of Rivastigmine (the Compound Represented by Formula (VIII))

117.5 ml acetone and 2.83 g (18.9 mmol) L-tartaric acid were added into 4.72 g (18.9 mmol) the compound represented by formula (VII). The mixture was heated to 40, followed by adding 11.8 ml methanol, and refluxed for 40 min. After the mixture was cooled to 40, seed crystal was added was and the mixture was stirred at room temperature for 2 hours. Then the mixture was settled in an ice bath for 5 hours followed by standing in a refrigerator overnight. After filtering and drying in a vacuum oven at 40 for 9 hours, white crystal (5.89 g) was obtained with a yield of 78%. HPLC purity=99.8%, ee %=99.8%

Optical rotation $[\alpha]^{20}_D = +6.0°$, C=5, ethanol; mp 122.3-124.1

$^1$H NMR (CDCl$_3$) δ ppm: 1.24, 1.16 (2×t, 3H), 1.67 (d, 3H), 2.65 (s, 6H), 2.96, 3.05 (2×s, 3H), 3.37, 3.45 (2×q, 2H), 4.34 (q, 1H), 4.47 (s, 2H), 7.14 (t, 1H), 7.20 (s, 1H), 7.28 (d, 1H), 7.39 (t, 1H); MS (ESI) m/z: 251.2.

EXAMPLE 11

Preparation of Rivastigmine (the Compound Represented by Formula (VIII))

50 ml acetone and 2.83 g (18.9 mmol) L-tartaric acid were added into 4.72 g (18.9 mmol) the compound represented by formula (VII). The mixture was heated to reflux for 40 min. After the mixture was cooled to 40, seed crystal was added was and the mixture was stirred at room temperature for 2 hours. Then the mixture was settled in an ice bath for 5 hours followed by standing in a refrigerator overnight. After filtering and drying in a vacuum oven at 40 for 9 hours, white crystal (5.74 g) was obtained with a yield of 76%. HPLC purity=99.8%, ee %=99.8%

Optical rotation $[\alpha]^{20}_D = +6.0°$, C=5, ethanol; mp 122.3-124.1

$^1$H NMR (CDCl$_3$) δ ppm: 1.24, 1.16 (2×t, 3H), 1.67 (d, 3H), 2.65 (s, 6H), 2.96, 3.05 (2×s, 3H), 3.37, 3.45 (2×q, 2H), 4.34 (q, 1H), 4.47 (s, 2H), 7.14 (t, 1H), 7.20 (s, 1H), 7.28 (d, 1H), 7.39 (t, 1H); MS (ESI) m/z: 251.2.

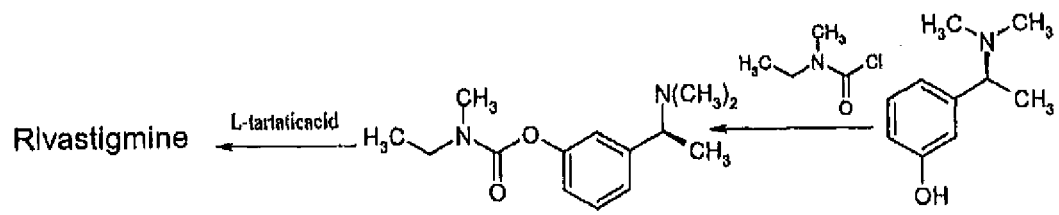

What is claimed is:

1. A compound having a structure of formula (IV):

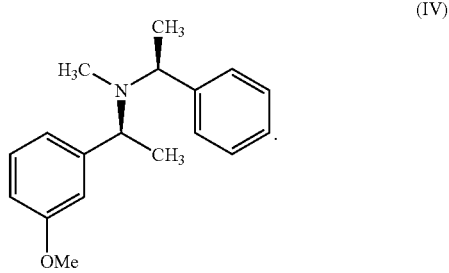

(IV)

2. A process of preparing a compound of formula (II)

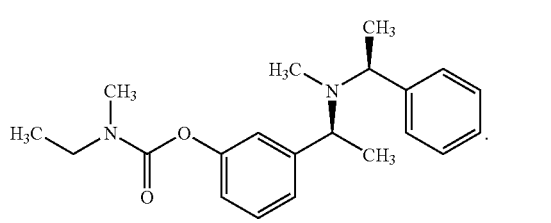

(II)

comprising the steps of
a) methylating a compound of formula (III) to provide a compound of formula (IV)

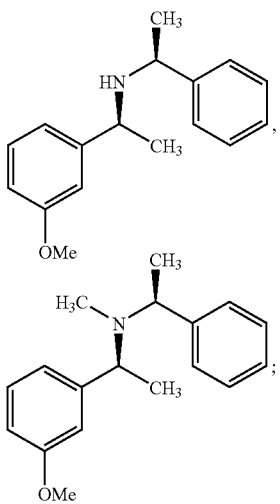

b) demethylating the compound of formula (IV) to obtain a compound of formula (V)

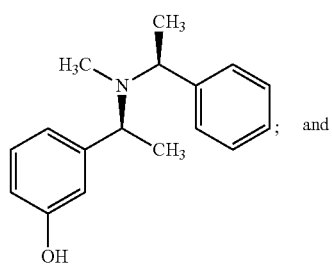

; and c) carrying out a condensation reaction of the compound of formula (V) and N-methyl-N-ethyl-amino formacyl chloride in the presence of at least one phase-transfer catalyst selected from the group consisting of tetrabutyl ammonium bromide, tetraethyl ammonium bromide, tetrabutyl ammonium iodide and triethyl benzyl ammonium chloride to provide a compound of formula (II).

3. The process of claim 2, wherein the methylation reaction of step a) is a Eschweiler-Clarke reaction or methyl iodide or dimethyl sulphate is used as a methylation agent in the methylation reaction of step a).

4. The process of claim 2, wherein the demethylation reaction of step b) is carried out in hydrobromic acid and at least one phase-transfer catalyst is used, and said at least one phase-transfer catalyst is selected from the group consisting of tetrabutyl ammonium bromide, tetraethyl ammonium bromide, tetrabutyl ammonium iodide and triethyl benzyl ammonium chloride.

5. The process of claim 2, wherein at least one basic reagent is used during the condensation reaction of step c), and at least one basic reagent is selected from the group consisting of sodium carbonate, potassium carbonate, sodium amide and sodium hydride, sodium methanol, sodium ethanol and potassium t-butanol, triethylamine, pyridine, quinoline and diisopropylethylamine.

6. The process of claim 2, wherein at least one inert solvent is used in the condensation reaction of step c), and at least one inert solvent is selected from the group consisting of tetrahydrofuran, ethyl ether, ethylene glycol dimethyl ether, dioxane, dimethyl tetrahydrofuran, benzene, toluene, xylene, dichloromethane, trichloromethane, dichloroethane, dimethylformamide, dimethyl acetamide and acetone.

\* \* \* \* \*

UNITED STATES PATENT AND TRADEMARK OFFICE
CERTIFICATE OF CORRECTION

PATENT NO.        : 8,324,429 B2                        Page 1 of 2
APPLICATION NO.   : 12/812347
DATED             : December 4, 2012
INVENTOR(S)       : Zhang et al.

It is certified that error appears in the above-identified patent and that said Letters Patent is hereby corrected as shown below:

On Title Page:
Item 73, Assignees: Please correct "Zhejian Hisun Pharmaceutical Co., Ltd. (CN)"
to read -- Zhejiang Hisun Pharmaceutical Co., Ltd. (CN) --

In the Specification:
Column 1, Line 63: Please correct the drawing below:

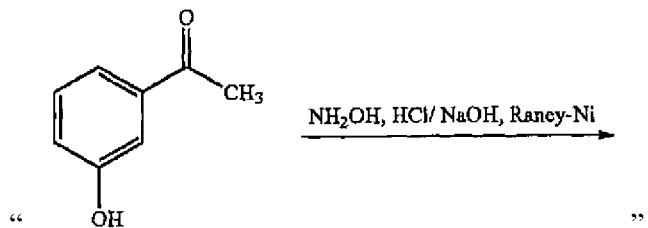

to read:

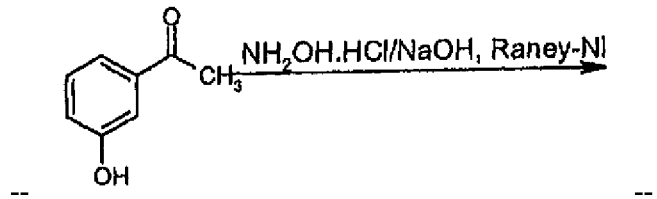

Columns 3 and 4: Please correct the drawing below:

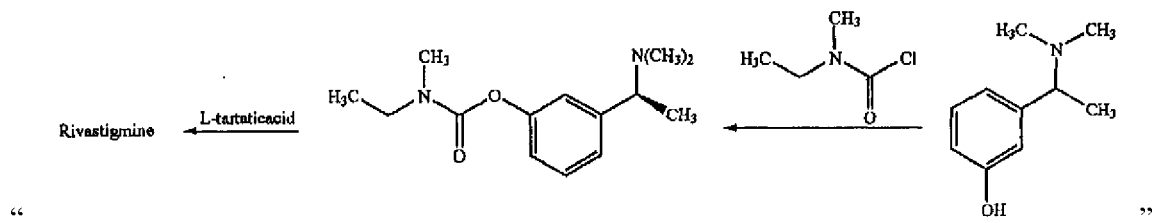

Signed and Sealed this
Sixth Day of August, 2013

Teresa Stanek Rea
*Acting Director of the United States Patent and Trademark Office*

CERTIFICATE OF CORRECTION (continued)

to read: